United States Patent [19]

Fukui et al.

[11] 4,387,038
[45] Jun. 7, 1983

[54] 4-(TRANS-4'-ALKYLCYCLOHEXYL) BENZOIC ACID 4'''-CYANO-4''-BIPHENYLYL ESTERS

[75] Inventors: Masahiro Fukui; Hiromichi Inoue; Yasuyuki Goto, all of Yokohamashi, Japan

[73] Assignee: Chisso Corporation, Osaka, Japan

[21] Appl. No.: 278,204

[22] Filed: Jun. 26, 1981

[30] Foreign Application Priority Data

Jul. 15, 1980 [JP] Japan .................. 55/96475

[51] Int. Cl.$^3$ .................. C09K 3/34; G02F 1/13; C07C 121/60; C07C 121/46; C07C 69/773; C07C 69/78
[52] U.S. Cl. .................. 252/299.63; 260/465 D; 350/350 R
[58] Field of Search .................. 252/299.63, 299.66, 252/299.65; 260/465 D, 465 R, 465 F; 350/350 R

[56] References Cited

U.S. PATENT DOCUMENTS

| 4,013,582 | 3/1977 | Lavrilovic | 252/299.63 |
| 4,029,595 | 6/1977 | Ross et al. | 252/299.62 |
| 4,113,647 | 9/1978 | Coates et al. | 252/299.62 |
| 4,222,887 | 9/1980 | Matsufuji | 252/299.63 |
| 4,227,778 | 10/1980 | Raynes | 252/299.64 |
| 4,228,030 | 10/1980 | Cole, Jr. | 252/299.63 |
| 4,229,315 | 10/1980 | Krause et al. | 252/299.63 |
| 4,253,740 | 3/1981 | Raynes et al. | 252/299.66 |
| 4,261,652 | 4/1981 | Gray et al. | 252/299.62 |
| 4,285,829 | 8/1981 | Eidenschink et al. | 252/299.63 |

FOREIGN PATENT DOCUMENTS

| 22882 | 1/1981 | European Pat. Off. | 252/299.63 |
| 23730 | 2/1981 | European Pat. Off. | 252/299.63 |
| 54-99785 | 8/1979 | Japan | 252/299.63 |
| 2031010 | 4/1980 | United Kingdom | 252/299.66 |

OTHER PUBLICATIONS

Gray, C. W., Mol. Cryst. Liq. Cryst., vol. 63, pp. 3–18 (1981).
Coates, A. et al., Mol. Cryst. Liq. Cryst., vol. 37, pp. 249–262 (1976).
Gray, C. W. et al., Mol. Cryst. Liq. Cryst., vol. 53, pp. 147–166 (1979).
Dewar, M. J. S. et al., J. A. C. S., vol. 92, No. 6, pp. 1582–1586 (1970).
"A Review of Some Liquid Crystal Materials and Their Properties", G. W. Gray, The 3rd Symposium on Liquid Crystals, Nov. 1977, pp. 18–19.

Primary Examiner—Teddy S. Gron
Attorney, Agent, or Firm—Wenderoth, Lind & Ponack

[57] ABSTRACT

Novel compounds, 4-(trans-4'-alkylcyclohexyl)benzoic acid 4'''-cyano-4''-biphenylyl esters expressed by the general formula

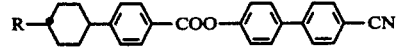

wherein R represents an alkyl group having 1 to 10 carbon atoms, and liquid crystal compositions comprising at least one of the esters are provided.

Liquid crystal compositions containing the compounds have practical superior characteristic properties and also good stability.

7 Claims, No Drawings

-continued

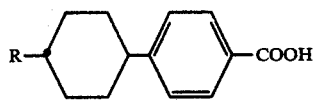

Monobromobenzene and a 4-alkylcyclohexanone are subjected to Grignard reaction to obtain a 4-alkyl-1-phenylcyclohexanol, which is then subjected to a hydrogenation reaction in ethanol in the presence of Raney nickel catalyst to obtain a mixture of the cis-and trans-forms of 4-alkyl-1-phenylcyclohexane. This mixture is distilled under reduced pressure and then subjected to Friedel-Crafts reaction together with acetyl chloride in the presence of aluminum chloride employing methylene chloride as solvent to obtain a 4-(4'-alkylcyclohexyl) acetophenone. Aluminum chloride is removed from this product in a conventional manner and the resulting material is distilled under reduced pressure to obtain a 4-(trans-4'-alkylcyclohexyl) acetophenone separated from its cis-form, which is then subjected to an oxidation reaction with sodium hypobromite in a mixed solvent of water/dioxane at room temperature for several hours, followed by acidifying the reaction system to deposit crystals, which are then recrystallized from acetic acid to obtain a 4-(trans-4'-alkylcyclohexyl) benzoic acid.

The preparation of the compounds of the present invention and their use will be described below in detail by way of the following Examples.

EXAMPLE 1

Preparation of 4-(trans-4'-pentylcyclohexyl) benzoic acid 4'''-cyano-4''-biphenylyl ester 4-(Trans-4'-pentylcyclohexyl) benzoic acid (7 g) and thionyl chloride (4.6 g) are fed into a 100 ml capacity egg-plant type flask and dissolved together on heating and further subjected to reflux for 30 minutes, followed by distilling off excess thionyl chloride and dissolving the resulting residue in 20 ml of toluene. On the other hand, 4-hydroxy-4'-cyanobiphenyl (5 g) and dry pyridine (10 g) are fed into a 200 ml capacity three-neck flask and dissolved together with stirring, followed by adding 50 ml of dry toluene and stirring to obtain a uniform solution. To this solution is gradually dropwise added a toluene solution of the acid chloride of 4-(trans-4'-pentylcyclohexyl)benzoic acid obtained above, through a dropping funnel. After the addition, the contents are warmed to 60° C. on a water bath, kept for 1.5 hour and cooled. Toluene (200 ml) and water (20 ml) are added, and the mixture is transferred into a separating funnel, followed by washing with an acid and then an alkali, further washing with water and making the liquid neutral. The resulting toluene layer is separated and active carbon (2 g) is added, followed by warming to 70° C. keeping for about 15 minutes, cooling and removing the active carbon by suction-filtering. Water is azeotropically removed from the layer by distilling off a part of the toluene under atmospheric pressure, followed by passing the resulting liquid through an activated alumina layer, completely distilling off toluene and recrystallizing the remaining solid from benzene (5 ml) to obtain colorless, acicular crystals as objective product (4.8 g), which had a melting point (C-N point) of 128° C. and a transparent point of 280° C. or higher. (The probable value through extrapolation by means of mix-melting with a liquid crystal of the cyanobiphenyl group corresponds to 460° C.) Further the elemental analysis of this product was in accord with the theoretical values as follows:

| | Analytical value (%) | Theoretical value (%) (as $C_{31}H_{33}NO_2$) |
|---|---|---|
| C | 82.7 | 82.45 |
| H | 7.2 | 7.37 |
| N | 7.2 | 7.09 |

EXAMPLES 2–5

Example 1 was repeated except that 4-(trans-4'-pentylcyclohexyl) benzoic acidin Example 1 was replaced by four 4-(trans-4'-alkylcyclohexyl) benzoic acids having different alkyl groups, respectively, to obtain ester compounds of the present invention corresponding to these benzoic acids. The esters were colorless, acicular crystals. Their C-N point, N-I point, etc. are as follows:

4-(trans-4'-propylcyclohexyl) benzoic acid 4'''-cyano-4''-biphenylyl ester
   C-N point: 165° C., N-I point: 280° C. or higher 4-(trans-4'-heptylcyclohexyl) benzoic acid 4'''-cyano-4''-biphenylyl ester
   m.p. (C-S point): 115° C., S-N point, 209° C., N-I point: 280° C. or higher (the probable value through extrapolation as in Example 1 was about 420° C.)

4-(trans-4'-ethylcyclohexyl) benzoic acid 4'''-cyano-4''-biphenylyl ester
   C-N point: 164° C., N-I point: 280° C. or higher 4-(trans-4'-butylcyclohexyl) benzoic acid 4'''-cyano-4''-biphenylyl ester
   C-N point: 129° C., N-I point: 280° C. or higher

EXAMPLE 6

A liquid crystal composition having the following composition was prepared:

| | |
|---|---|
| $C_5H_{11}$—⟨⟩—⟨⟩—CN | 45% by weight |
| $C_7H_{15}$—⟨⟩—⟨⟩—CN | 30% by weight |
| $C_8H_{17}O$—⟨⟩—⟨⟩—CN | 17% by weight |
| $C_7H_{15}$—⟨⟩—⟨⟩—COO—⟨⟩—⟨⟩—CN | 8% by weight |

This liquid crystal composition had a nematic liquid crystal temperature range of −10° to +66° C. and a viscosity of 48 cp at 20° C. This composition was sealed between two glass base plates equipped with transparent electrodes each coated with $SiO_2$ film and subjected to a surface orientation treatment by rubbing to prepare a TN cell 10 μm thick, and its actuation voltages were measured to give a threshold voltage of 1.6 V and a saturation voltage of 2.2 V.

For comparison,

4-(TRANS-4'-ALKYLCYCLOHEXYL) BENZOIC ACID 4'''-CYANO-4''-BIPHENYLYL ESTERS

BACKGROUND OF THE INVENTION

1. Field of the Invention

This invention relates to novel organic compounds. More particularly it relates to novel liquid crystal compounds useful as a component of liquid crystal materials.

2. Description of the Prior Art

Liquid crystal substances have already been broadly used for liquid crystal display elements of the so-called twisted nematic mode utilizing nematic liquid crystals of a twisted liquid crystal arrangement. They have also been used for color display elements employing a liquid crystal of a mixture of liquid crystals containing a suitable dyestuff, utilizing a guest-host effect, and have been used for DSM display elements utilizing a dynamic scattering effect, display elements utilizing a cholesteric phase-nematic phase transition, DAP type display elements utilizing an electrically controlled birefringence effect, etc.

As to liquid crystal materials used for these display elements, no single compound has been found whose various characteristic properties such as liquid crystal temperature range, actuation voltage, response performance, etc. endure practical uses; hence it is the present status that several kinds of liquid crystal compounds are mixed together to obtain those which endure practical uses.

SUMMARY OF THE INVENTION

The object of the present invention is to provide compounds useful as a component of liquid crystal compositions having practical superior characteristic properties and also good stability.

The present invention resides in:

4-(trans-4'-alkylcyclohexy)benzoic acid 4'''-cyano-4''-biphenylyl esters expressed by the general formula

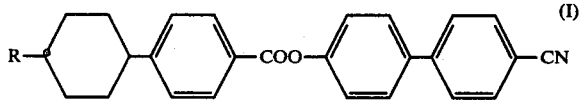

(I)

wherein R represents an alkyl group having 1 to 10 carbon atoms.

DETAILED DESCRIPTION OF THE INVENTION

The compounds of the present invention have a positive dielectric anisotropy, a broad liquid crystal temperature range, a very high transparent point and superior stability, but due to their high melting points, they cannot be used alone. However, they have a good compatibility with other liquid crystal compounds such as liquid crystals of Schiff's base group, azoxy group, benzoic acid phenyl ester group, cyclohexanecarboxylic acid phenyl ester group, cyclohexanecarboxylic acid cyclohexyl ester group, biphenyl group (for example, a 4-alkyl-4'-cyanobiphenyl or 4-alkoxy-4'-cyanobiphenyl compound), phenylcyclohexane group, phenylpyrimidine group, phenylmetadioxane group, etc.; hence when they are mixed with these liquid crystals, they are useful as a high temperature liquid crystal component having a function of raising the transparent point of liquid crystal compositions to broaden their liquid crystal temperature ranges. Such an effectiveness of the compounds of the present invention is greater than those of 4-cyano-4''-pentyl-p-terphenyl, 4-cyano-4'-(trans-4''-pentylcyclohexyl)-biphenyl, etc. which have so far been well known as compounds having a similar function.

The compounds of the present invention can be prepared according to the following steps:

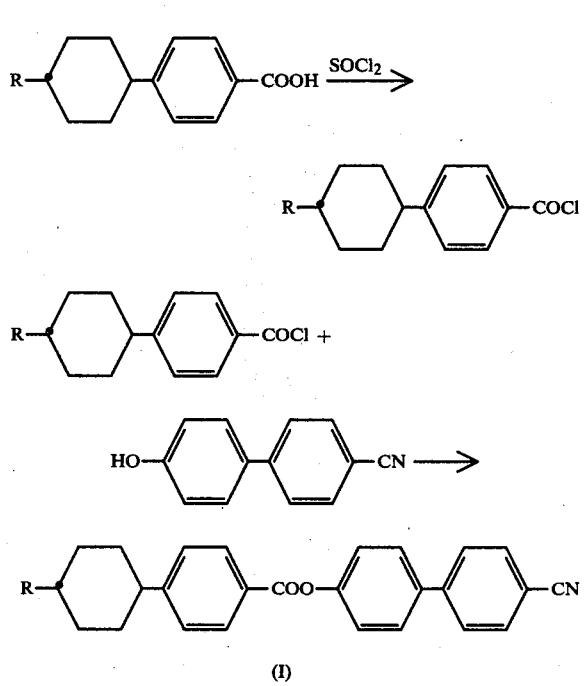

(I)

Namely, a 4-(trans-4'-alkylcyclohexyl)benzoic acid is reacted with thionyl chloride to obtain its acid chloride, which is then reacted with (4-hydroxy-4'-cyanobiphenyl in pyridine to obtain the objective 4-(trans-4'-alkylcyclohexyl)benzoic acid 4'''-4''-biphenylyl ester.

4-(Trans-4'-alkylcyclohexyl) benzoic acids as a starting material can be prepared through the following reaction course:

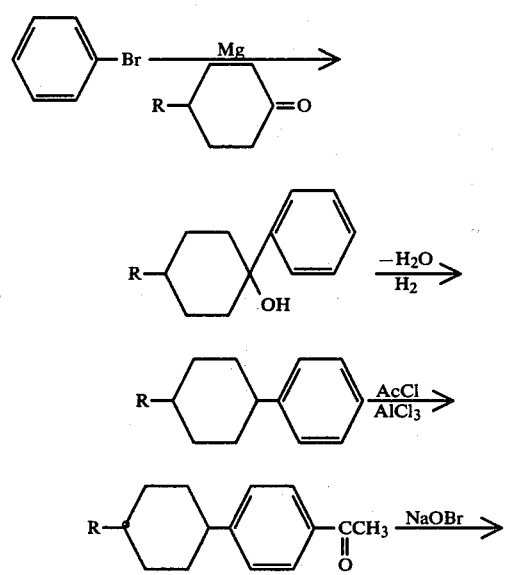

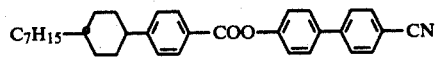

contained in this composition was replaced by

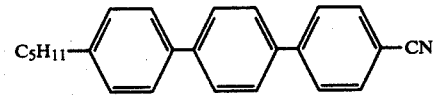

(30% by weight) which has been often used in known compositions. The resulting composition had a nematic liquid crystal range as narrow as −10° to 58° C. and a viscosity of 42 cp at 20° C. Its threshold voltage and saturation voltage measured under the same conditions as above were 1.6 V and 2.2 V, respectively.

EXAMPLE 7

A liquid crystal composition having the following composition was prepared:

| Structure | Amount |
|---|---|
| C₂H₅—⌬—COO—⌬—CN | 15% by weight |
| C₃H₇OCH₂CH₂O—⌬—COO—⌬—CN | 10% by weight |
| C₂H₅—⌬—⌬—CN | 25% by weight |
| C₃H₇—⌬—⌬—CN | 20% by weight |
| C₄H₉—(dioxane)—⌬—CN | 20% by weight |

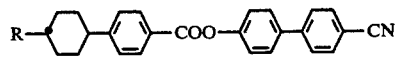

5% by weight

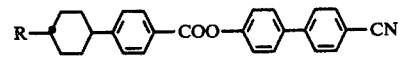

5% by weight

Its nematic liquid crystal range was −10° to +57.5° C. Its threshold voltage and saturation voltage obtained by sealing the composition in the same TN cell as in Example 6, followed by measurement, were 1.00 V and 1.45 V, respectively.

We claim:

1. A 4-(trans-4'-alkylcyclohexyl)benzoic acid 4'''-cyano-4''-biphenylyl ester expressed by the formula

R—⌬—⌬—COO—⌬—⌬—CN wherein R represents an alkyl group having 1 to 10 carbon atoms.

2. An ester according to claim 1 wherein R is an alkyl group having 2 to 7 carbon atoms.

3. An ester according to claim 1 wherein R is $C_5H_{11}$.

4. An ester according to claim 1 wherein R is $C_7H_{15}$.

5. A liquid crystal composition comprising a mixture of compounds at least one of which is a 4-(trans-4'-alkylcyclohexyl)benzoic acid 4'''-cyano-4''-biphenylyl ester expressed by the formula

R—⌬—⌬—COO—⌬—⌬—CN wherein R represents an alkyl group having 1 to 10 carbon atoms.

6. A liquid crystal composition according to claim 5, containing at least one 4-alkyl-4' cyanobiphenyl compound.

7. A liquid crystal composition according to claim 5, containing at least one 4-alkoxy-4'-cyanobiphenyl compound.

* * * * *